(12) United States Patent
Park et al.

(10) Patent No.: US 10,294,334 B2
(45) Date of Patent: *May 21, 2019

(54) METHOD FOR PREPARING SUPER ABSORBENT RESIN

(71) Applicant: LG Chem, Ltd., Seoul (KR)

(72) Inventors: Bo-Hee Park, Daejeon (KR); Young-Sam Kim, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/322,580

(22) PCT Filed: Jan. 13, 2016

(86) PCT No.: PCT/KR2016/000349
§ 371 (c)(1),
(2) Date: Dec. 28, 2016

(87) PCT Pub. No.: WO2016/175428
PCT Pub. Date: Nov. 3, 2016

(65) Prior Publication Data
US 2017/0137581 A1 May 18, 2017

(30) Foreign Application Priority Data
Apr. 28, 2015 (KR) .................. 10-2015-0059462

(51) Int. Cl.
*C08J 3/075* (2006.01)
*C08F 2/44* (2006.01)
(Continued)

(52) U.S. Cl.
CPC .............. *C08J 3/075* (2013.01); *A61L 15/60* (2013.01); *C08F 2/10* (2013.01); *C08F 2/44* (2013.01);
(Continued)

(58) Field of Classification Search
CPC ... C08J 3/075; C08J 9/006; C08J 9/125; C08J 3/245; C08J 9/008; C08J 2205/022;
(Continued)

(56) References Cited

U.S. PATENT DOCUMENTS 5,087,656 A 2/1992 Yoshinaga et al.
2010/0112200 A1 5/2010 Barthel et al.
(Continued)

FOREIGN PATENT DOCUMENTS

CN 101679760 A 3/2010
EP 3078678 A1 10/2016
(Continued)

OTHER PUBLICATIONS

Lee et al., machine English translation of WO 2015/084059 (Jun. 2015).*

(Continued)

*Primary Examiner* — Jessica M Roswell
(74) *Attorney, Agent, or Firm* — Lerner, David, Littenberg, Krumholz & Mentlik, LLP

(57) ABSTRACT

The present invention relates to a method for preparing a superabsorbent polymer including a) preparing a hydrogel phase polymer by thermopolymerizing or photopolymerizing a monomer composition including a water-soluble ethylenically unsaturated monomer and a polymerization initiator; b) chopping the hydrogel phase polymer; c) adding particles having properties of the following i) and ii) to the chopped hydrogel phase polymer; d) chopping the particle-added hydrogel phase polymer again; e) drying the hydrogel phase polymer; f) milling the dried hydrogel phase polymer; g) adding a surface crosslinking agent to the milled hydrogel phase polymer; and h) carrying out a surface crosslinking reaction.

i) BET specific surface area of 300 $m^2/g$ to 1500 $m^2/g$,
ii) Porosity of 50% or greater.

20 Claims, 2 Drawing Sheets

(51) Int. Cl.

| | |
|---|---|
| *C08F 2/10* | (2006.01) |
| *C08K 3/22* | (2006.01) |
| *C08K 3/04* | (2006.01) |
| *C08K 5/00* | (2006.01) |
| *C08J 3/24* | (2006.01) |
| *C08J 9/00* | (2006.01) |
| *A61L 15/60* | (2006.01) |
| *C08J 9/28* | (2006.01) |
| *C08K 3/36* | (2006.01) |

(52) U.S. Cl.
CPC .............. *C08J 3/245* (2013.01); *C08J 9/0066* (2013.01); *C08J 9/286* (2013.01); *C08K 3/22* (2013.01); *C08K 5/00* (2013.01); *C08J 2201/026* (2013.01); *C08J 2201/0504* (2013.01); *C08J 2205/022* (2013.01); *C08J 2333/02* (2013.01); *C08K 3/36* (2013.01); *C08K 2201/005* (2013.01)

(58) Field of Classification Search
CPC ...... C08J 2333/02; C08J 9/0066; C08J 9/286; C08J 2201/026; C08J 2201/0504; C08K 2201/005; C08K 3/36; C08K 3/22; C08K 5/00; A61L 15/60; C08F 2/44; C08F 2/10
See application file for complete search history.

(56) References Cited

U.S. PATENT DOCUMENTS

| | | |
|---|---|---|
| 2014/0193641 A1 | 7/2014 | Torii et al. |
| 2014/0378926 A1 | 12/2014 | Ota et al. |

FOREIGN PATENT DOCUMENTS

| | | | | |
|---|---|---|---|---|
| EP | 3165564 A1 | 5/2017 | | |
| EP | 3290447 A1 | 3/2018 | | |
| JP | H08253597 A | 10/1996 | | |
| JP | 2010253283 A | 11/2010 | | |
| JP | 2012217599 A | 11/2012 | | |
| KR | 20140038998 A | 3/2014 | | |
| KR | 101507287 B1 | 3/2015 | | |
| WO | WO-2015-084059 | * | 6/2015 | ................ C08F 2/00 |

OTHER PUBLICATIONS

Lee et al., machine English translation of KR 10-1057287 (corresponding to WO 2015/084059) (Year: 2015).*
International Search Report from PCT/KR2016/000349, dated Jul. 1, 2016.
Extended European Search Report including Written Opinion for Application No. EP 16786615.1 dated May 4, 2018.

\* cited by examiner

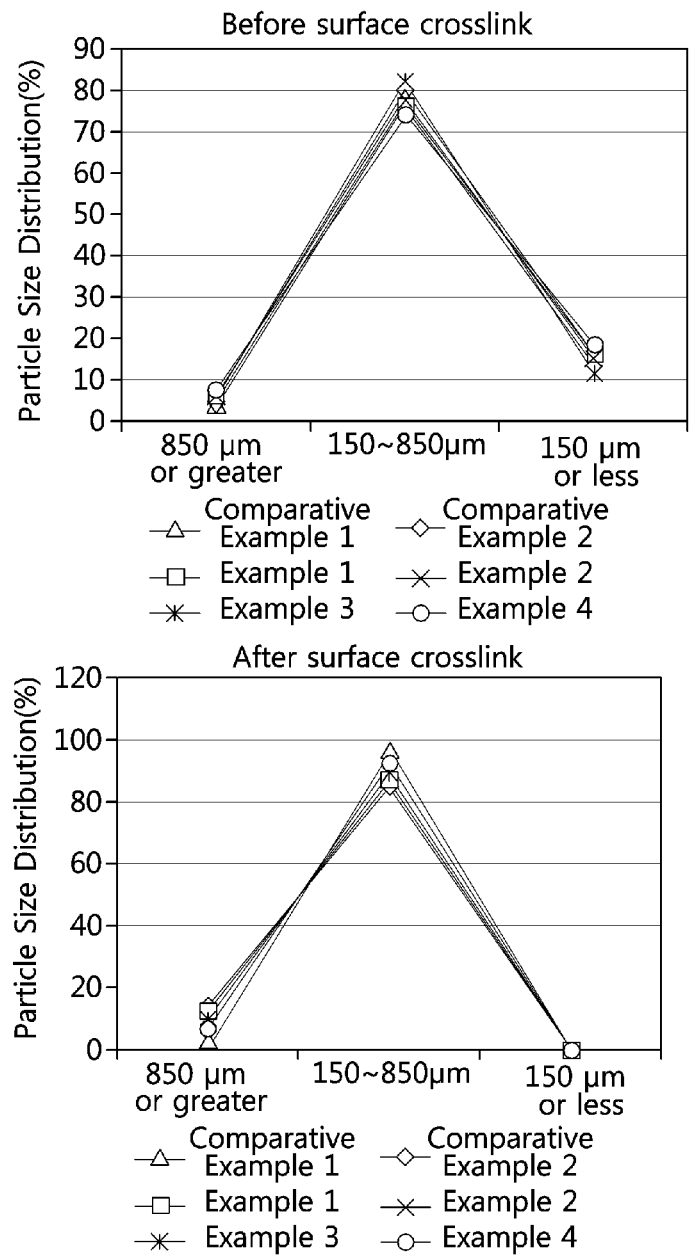
[FIG. 1]

[FIG. 2]
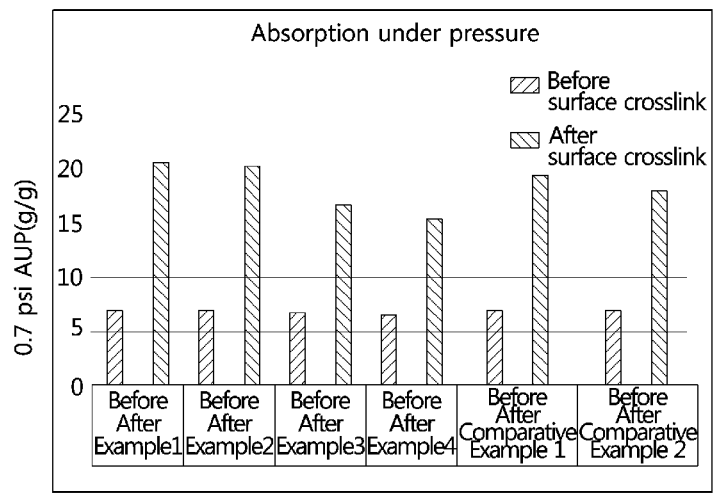
[FIG. 3]
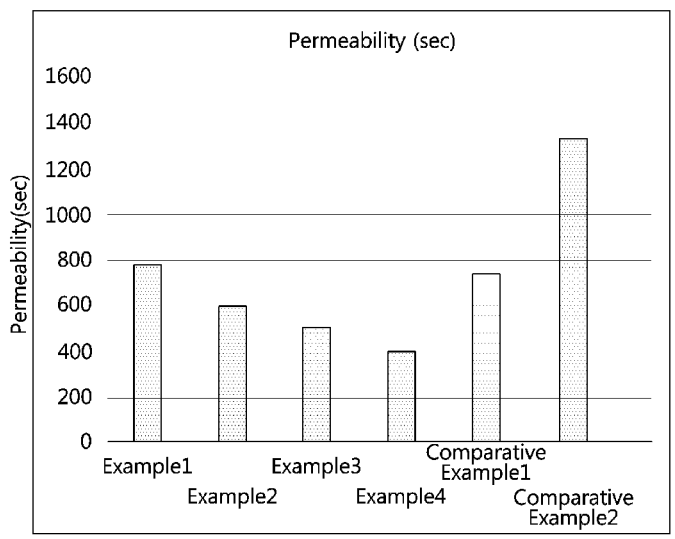

METHOD FOR PREPARING SUPER ABSORBENT RESIN

CROSS-REFERENCE TO RELATED APPLICATION

This application is a national phase entry under 35 U.S.C. § 371 of International Application No. PCT/KR2016/000349, filed Jan. 13, 2016, which claims priority to Korean Patent Application No. 10-2015-0059462, filed Apr. 28, 2015, the disclosures of which are incorporated herein by reference.

TECHNICAL FIELD

The present invention relates to a method for preparing a superabsorbent polymer, and in particular, to a method for preparing a superabsorbent polymer on which super-hydrophobic particles are introduced.

BACKGROUND ART

Superabsorbent polymers (SAPs) refer to a synthetic polymer material having a function capable of absorbing 500 to 1000 times of moisture in a weight with respect to the polymer weight itself, and have started to be commercialized as sanitary products, and are widely used currently as soil repair materials for gardening, water stop materials for civil engineering and construction, sheets for raising seedlings, freshkeeping materials in food distribution fields, and materials for fomentation and the like in addition to personal hygiene items such as paper diapers for children and sanitary napkins.

In such superabsorbent polymer preparation processes, water is a polymerization medium and the use is diverse such as facilitating crosslinking liquid dispersion in a surface crosslinking process. In addition, residual moisture in a final product performs a role of an antistatic agent for polymers and a plasticizer, suppresses formation of very small superabsorbent polymer dusts in application processes, and prevents milling of SAP particles. However, when water is added to a superabsorbent polymer even in a small amount, stickiness on a surface of the polymer generally increases due to water absorbed on the surface, and irreversible agglomeration between the superabsorbent polymer particles occurs. Such a stickiness increase and agglomeration reduce processability such as a load increase in preparation and application processes, which resultantly causes a particle size increase, physical property decline and productivity decline of superabsorbent polymers. So far, researches on superabsorbent polymers have focused on polymerization processes and absorption capacity enhancement obtained therethrough, and surface crosslink for increasing surface properties or absorption under pressure of the superabsorbent polymers, and researches on the changes in surface properties have been carried out for enhancing permeability, or solving some problems such as preventing hardening of superabsorbent polymers when being stored (anti-caking).

Specifically, superabsorbent polymers have a crosslinked three-dimensional network structure and are swollen by water, but have a structure insoluble in water, and accordingly, core/shell structure technologies increasing crosslink density on the surface have been developed for high absorption under pressure and permeability properties of superabsorbent polymers. In such technologies, final physical properties are determined depending on various conditions such as crosslink density adjustment, uniform shell formation and shell thickness adjustment. With the recent development of pulpless diapers, physical properties of superabsorbent polymers themselves are directly connected to physical properties of diapers, and importance of superabsorbent polymers has gradually grown.

Particularly, a surface crosslinking agent is dissolved in water to be used in a surface crosslinking process of a superabsorbent polymer, and although the water used herein is a solvent enabling the crosslinking agent to be absorbed on the surface of the superabsorbent polymer, it may increase stickiness on the superabsorbent polymer surface by inducing non-uniform penetration and become a reason for partial agglomeration. Accordingly, for solving such a problem, an organic solvent is excessively used for controlling the absorbed amount and facilitating dispersion of the crosslinking agent into more particles, and this environmentally requires additional processes such as removing the residual organic solvent, and particularly, is not suitable to be used for diapers for newborn babies.

In this regard, Korean Patent Application Laid-Open Publication No. 2014-0038998 discloses a method for preparing absorbent polymer powder, however, the absorbent polymer powder has a limit not only in absorption under pressure and permeability properties, but in reducing an amount of a surface crosslinking agent used. Consequently, the development of a method for preparing a superabsorbent polymer having excellent absorption under pressure and permeability properties while reducing an amount of a surface crosslinking agent used for enhancing physical properties of the superabsorbent polymer has been required.

DISCLOSURE

Technical Problem

The present invention has been made in view of the above, and an object of the present invention is to provide a method for preparing a superabsorbent polymer capable of, by modifying a surface of the superabsorbent polymer to be hydrophobic and thereby reducing viscosity and a degree of agglomeration caused by moisture absorption, uniform surface crosslink without using a liquid surface crosslinking agent containing an organic solvent used in the art while decreasing a load in a manufacturing process through processability enhancement, facilitating particle size and physical property control, and satisfying both high moisture content and high processability.

Technical Solution

One embodiment of the present invention provides a method for preparing a superabsorbent polymer including a) preparing a hydrogel phase polymer by thermopolymerizing or photopolymerizing a monomer composition including a water-soluble ethylenically unsaturated monomer and a polymerization initiator;

b) chopping the hydrogel phase polymer;

c) adding particles having properties of the following i) and to the chopped hydrogel phase polymer;

d) chopping the particle-added hydrogel phase polymer again;

e) drying the hydrogel phase polymer;

f) milling the dried hydrogel phase polymer;

g) adding a surface crosslinking agent to the milled hydrogel phase polymer; and h) carrying out a surface crosslinking reaction, wherein i) BET specific surface area of 300 $m^2$/g to 1500 $m^2$/g and porosity of 50% or greater.

Advantageous Effects

A method for preparing a superabsorbent polymer according to the present invention has advantages in that the method modifies a surface of a superabsorbent polymer to be hydrophobic and thereby reduces viscosity and a degree of agglomeration caused by moisture absorption, and as a result, decreases a load in a manufacturing process through processability enhancement, facilitates particle size and physical property control, and satisfies both high moisture content and high processability, and is also capable of uniform surface crosslink while significantly reducing an amount of a surface crosslinking liquid introduced compared to amounts used in the art, and obtaining an anti-caking effect and permeability enhancement without post-processing.

DESCRIPTION OF DRAWINGS

FIG. 1 is a graph showing results of identifying particle size distribution prior to and after milling a superabsorbent polymer of the present invention.

FIG. 2 is a graph showing results of measuring absorption under pressure of a superabsorbent polymer of the present invention.

FIG. 3 is a graph showing results of measuring permeability of a superabsorbent polymer of the present invention.

BEST MODE

Hereinafter, the present invention will be described in detail.

A method for preparing a superabsorbent polymer according to the present invention includes a) preparing a hydrogel phase polymer by thermopolymerizing or photopolymerizing a monomer composition including a water-soluble ethylenically unsaturated monomer and a polymerization initiator; b) chopping the hydrogel phase polymer; c) adding particles having properties of the following i) and to the chopped hydrogel phase polymer; d) chopping the particle-added hydrogel phase polymer again; e) drying the hydrogel phase polymer; f) milling the dried hydrogel phase polymer; g) adding a surface crosslinking agent to the milled hydrogel phase polymer; and h) carrying out a surface crosslinking reaction.

i) BET specific surface area of 300 $m^2/g$ to 1500 $m^2/g$, ii) Porosity of 50% or greater First, the method for preparing a superabsorbent polymer according to the present invention goes through a step of a) preparing a hydrogel phase polymer by thermopolymerizing or photopolymerizing a monomer composition including a water-soluble ethylenically unsaturated monomer and a polymerization initiator.

For preparing a superabsorbent polymer of the present invention, the polymer may be prepared using steps and methods commonly used in the art. Specifically, in the method for preparing a superabsorbent polymer of the present invention, the monomer composition includes a polymerization initiator, and depending on the polymerization method, may include a photopolymerization initiator when using a photopolymerization method, and may include a thermopolymerization initiator when using a thermopolymerization method. However, even when using a photopolymerization method, a thermopolymerization initiator may be additionally included since a certain amount of heat is generated from ultraviolet radiation and the like, and a certain degree of heat is generated as the polymerization reaction, an exothermic reaction, progresses.

The thermopolymerization initiator used in the method for preparing a superabsorbent polymer according to the present invention is not particularly limited, and one or more selected from the initiator group consisting of persulfate-based initiators, azo-based initiators, hydrogen peroxide, and ascorbic acid may be preferably used. Specifically, examples of the persulfate-based initiator may include sodium persulfate ($Na_2S_2O_8$), potassium persulfate ($K_2S_2O_8$), ammonium persulfate (($NH_4)_2S_2O_8$) and the like, and examples of the azo-based initiator may include 2,2-azobis(2-amidinopropane)dihydrochloride, 2,2-azobis-(N,N-dimethylene)isobutyramidinedihydrochloride, 2-(carbamoylazo)isobutylonitril, 2,2-azobis[2-(2-imidazolin-2-yl)propane]dihydrochloride, 4,4-azobis-(4-cyanovaleric acid) and the like.

In addition, the photopolymerization initiator used in the method for preparing a superabsorbent polymer according to the present invention is not particularly limited, and one or more selected from the group consisting of benzoin ether, dialkyl acetophenone, hydroxyl alkylketone, phenyl glyoxylate, benzyl dimethyl ketal, acyl phosphine and α-aminoketone may be preferably used. Meanwhile, specific examples of the acyl phosphine may include commercialized lucirin TPO, that is, 2,4,6-trimethyl-benzoyl-trimethyl phosphine oxide may be used.

Furthermore, in the method for preparing a superabsorbent polymer according to the present invention, the water-soluble ethylenically unsaturated monomer is not particularly limited as long as it is a monomer commonly used in superabsorbent polymer preparation, and preferably, any one or more selected from the group consisting of anionic monomers and salts thereof, nonionic-based-hydrophilic group-containing monomers, and amino group-containing unsaturated monomers and quaternary compounds thereof. Specifically, any one or more selected from the group consisting of anionic monomers such as acrylic acid, methacrylic acid, maleic anhydride, fumaric acid, crotonic acid, itaconic acid, 2-acryloylethanesulfonic acid, 2-methacryloylethanesulfonic acid, 2-(meth)acryloylpropanesulfonic acid or 2-(meth)acrylamide-2-methylpropanesulfonic acid, and salts thereof; nonionic-based-hydrophilic group-containing monomers such as (meth)acrylamide, N-substituted (meth)acrylate, 2-hydroxyethyl (meth)acrylate, 2-hydroxypropyl (meth)acrylate, methoxypolyethylene glycol (meth)acrylate or polyethylene glycol (meth)acrylate; and amino group-containing unsaturated monomers such as (N,N)-dimethylaminoethyl (meth)acrylate or (N,N)-dimethylaminopropyl (meth)acrylamide, and quaternary compounds thereof may be preferably used, and acrylic acid or salts thereof may be more preferably used. When acrylic acid or salts thereof are used as a monomer, there is an advantage in that superabsorbent polymers having particularly enhanced absorption may be obtained.

In the method for preparing a superabsorbent polymer according to the present invention, the monomer composition may further include fine particles, that is, a polymer or polymer powder having particle sizes of less than 150 μm, in a certain amount in the prepared superabsorbent polymer powder for an effect of resources recycling, and specifically, the polymer or polymer powder having particle sizes of less than 150 μm may be added prior to the polymerization reaction of the monomer composition, or at the beginning, in the middle or at the end after starting the polymerization reaction. Herein, the amount capable of being added is not particularly limited, however, adding 1 part by weight to 10 parts by weight with respect to 100 parts by weight of the monomer included in the monomer polymer composition is preferable for preventing physical property decline of the finally prepared superabsorbent polymer.

Meanwhile, in the method for preparing a superabsorbent polymer according to the present invention, a concentration of the water-soluble ethylenically unsaturated monomer in the monomer composition may be properly selected and used considering time taken for polymerization and a reaction condition, and is preferably from 40% by weight to 55% by weight. The water-soluble ethylenically unsaturated monomer having a concentration of less than 40% by weight is disadvantageous in terms of economic feasibility, and when the concentration is greater than 55% by weight, milling efficiency may be low when milling the polymerized hydrogel phase polymer.

A method for preparing the hydrogel phase polymer by thermopolymerizing or photopolymerizing such a monomer composition is also not limited in the constitution as long as it is a commonly used polymerization method. Specifically, the polymerization method is largely divided into thermopolymerization and photopolymerization depending on a polymerization energy source. Common thermopolymerization may be carried out in a reactor having a stirring shaft such as a kneader and photopolymerization may be carried out in a reactor provided with a movable conveyer belt, however, the polymerization methods described above are one example, and the present invention is not limited to the above-mentioned polymerization methods.

For example, the hydrogel phase polymer obtained through thermopolymerization by supplying hot air to a reactor provided with a stirring shaft such as a kneader as described above or heating the reactor may be a hydrogel phase polymer, which is discharged to an outlet of the reactor, with a few centimeter to few millimeter form depending on the form of a stirring shaft provided in the reactor. Specifically, sizes of the obtained hydrogel phase polymer may vary depending on a concentration and an injection rate of the injected monomer composition, and a hydrogel phase polymer having particle sizes of 2 mm to 50 mm may be commonly obtained.

In addition, when carrying out photopolymerization in a reactor provided with a movable conveyer belt as described above, a hydrogel phase polymer commonly obtained may be a sheet-shaped hydrogel phase polymer having a width of the belt. Herein, a thickness of the polymer sheet may vary depending on a concentration and an injection rate of the injected monomer composition, however, supplying the monomer composition so as to obtain a sheet-shaped polymer having a thickness of 0.5 cm to 5 cm is normally preferable. Supplying the monomer composition so as to obtain an excessively thin sheet-shaped polymer is not preferable since production efficiency is low, and when a sheet-shaped polymer has a thickness of greater than 5 cm, the polymerization reaction may not evenly occur over the whole thickness due to an excessively large thickness.

After that, the method for preparing a superabsorbent polymer according to the present invention goes through a step of b) chopping the hydrogel phase polymer. The chopping may be carried out by milling the hydrogel phase polymer so that the polymer particle sizes become 1 mm to 15 mm. Herein, milling the polymer to have particle sizes of less than 1 mm is technically difficult due to high moisture content of the hydrogel phase polymer and agglomeration between the milled particles may occur as well, and when milling the polymer to have particle sizes of greater than 15 mm, an efficiency increase effect of drying, which is carried out later, caused by the milling becomes insignificant.

A mill used in the chopping step is not limited in the constitution, and specifically, any one selected from the mill group consisting of a vertical pulverizer, a turbo cutter, a turbo grinder, a rotary cutter mill, a cutter mill, a disc mill, a shred crusher, a crusher, a chopper and a disc cutter may be included, however, the mill is not limited to the examples described above.

When going through the chopping step as above, a phenomenon of the polymer adhering to the mill surface may occur due to the polymer with high moisture content. Accordingly, additives and the like that may prevent the adhering may be additionally used in the milling in order to enhance efficiency of such a chopping step. Specific types of the additives that may be used are not limited in the constitution, and fine powder deaggregating agents such as steam, water, surfactants, and inorganic powder such as clay or silica; thermopolymerization initiators such as persulfate-based initiators, azo-based initiators, hydrogen peroxide and ascorbic acid, and crosslinking agents such as epoxy-based crosslinking agents, diol-based crosslinking agents, crosslinking agents including an acrylate including a difunctional group or a multifunctional group of trifunctional or higher and monofunctional compounds including a hydroxyl group, however, the additives are not limited thereto.

After that, the method for preparing a superabsorbent polymer according to the present invention goes through a step of c) adding particles having the following i) and ii) properties and a surface crosslinking agent to the hydrogel phase polymer.

i) BET specific surface area of 300 $m^2/g$ to 1500 $m^2/g$,
ii) Porosity of 50% or greater A superabsorbent polymer surface generally has hydrophilicity, and irreversible agglomeration occurs during drying after moisture absorption due to capillary force caused by water present between particles, hydrogen bonding, interparticular diffusion, Van der Waals force between particles or the like. Accordingly, water is also requisitely used in the polymerization and surface crosslinking processes of the superabsorbent polymer, and an internal load increases due to agglomeration caused therefrom, which may resultantly lead to equipment failure. In addition, the superabsorbent polymer in an agglomerated state as above has large particle sizes unsuitable for use, and accordingly, has a disadvantage in that a crushing process decreasing the particles to have proper particle sizes needs to be introduced. There is also a problem in that strong force is applied in the crushing process, and physical property decline caused by the superabsorbent polymer crushing may occur.

In view of the above, attempts to introduce various fine particles present on the superabsorbent polymer surface and capable of performing a role of preventing direct agglomeration of polymer particles have been tried, however, there is a disadvantage in that, although agglomeration is prevented, an absorption property of the superabsorbent polymer declines when excess fine particles are introduced.

In view of the above, the particles introduced to the superabsorbent polymer of the present invention have particle sizes of 2 nm to 50 µm. In addition, the particles may have a BET specific surface area of 300 $m^2/g$ to 1500 $m^2/g$, preferably of 500 $m^2/g$ to 1500 $m^2/g$ and more preferably of 700 $m^2/g$ to 1500 $m^2/g$. In addition, the particles may have superhydrophobicity with a contact angle of 125° or greater for water, preferably have superhydrophobicity of 140° or greater and more preferably have superhydrophobicity of 145° or greater. Furthermore, the particles have porosity of 50% or greater and preferably have porosity of 90% or greater. The method for preparing a superabsorbent polymer of the present invention uses particles having such properties, and therefore, is capable of not only reducing an influence of water present on the polymer surface, but significantly reducing agglomeration since porous superhydrophobic fine particles are used, and in addition to these, transmittance is readily enhanced and high moisture content may be readily obtained and maintained even when a relatively small amount of fine particles are used.

The particles added in the method for preparing a superabsorbent polymer according to the present invention are not limited in the components as long as the particles are a material having the following i) and properties, and specifically, inorganic oxides such as silica, alumina, titania ($TiO_2$) and carbon, inorganic compounds, organic polymers, ion exchange polymers, metals, metal salts and the like may be used, however, the particles are not limited thereto.

In addition, the fine particles are preferably added in 0.001 parts by weight to 1 part by weight with respect to 100 parts by weight of the superabsorbent polymer. When the fine particles are included in a smaller amount than the above-mentioned range, hydrophobicity of the superabsorbent polymer is not sufficient, and when the content is higher than the above-mentioned range, polymer processability declines.

As the method of adding the fine particles, a method of dispersing the fine particles in a monomer solution to use, a method of adding the fine particles to a hydrogel phase after polymerization and then dry mixing the result to a first dried polymer particles, a method of dispersing the fine particles in water or an organic solvent in which a surface crosslinking liquid is dissolved and mixing the result when crosslinking, a method of dry mixing the fine particles separately from water or an organic solvent in which a surface crosslinking liquid is dissolved when crosslinking, a method of dry mixing the fine particles to a surface crosslinked final product, or the like, may be used, however, the method is not limited thereto.

After that, the method for preparing a superabsorbent polymer according to the present invention goes through a step of d) chopping the particle-added hydrogel phase polymer again. The chopping in the d) step may be carried out in the same manner as in the b) step.

After that, the method for preparing a superabsorbent polymer according to the present invention goes through a step of e) drying the hydrogel phase polymer.

The hydrogel phase polymer obtained in the a) step normally has moisture content of 30% by weight to 60% by weight. Meanwhile, "moisture content" in the whole specification means a value subtracting a polymer weight in a dried state from a weight of a hydrogel phase polymer as moisture content occupied, with respect to the total weight of the hydrogel phase polymer. Specifically, "moisture content" is defined as a value calculated by, in a process drying a polymer from raising a temperature through infrared heating, measuring a weight decrease caused by moisture evaporation in the polymer, and herein, moisture content is measured under a drying condition of raising a temperature from room temperature to 180° C., and then maintaining the temperature at 180° C. with total drying time set at 20 minutes including 5 minutes of the temperature raising step.

A "drying temperature" in the whole specification may be defined as a temperature of a heating medium provided for drying or a temperature of a drying reactor including a heating medium and a polymer in a drying process, and a drying temperature of such a drying step may be from 150° C. to 250° C. and more preferably from 160° C. to 200° C.

When the drying temperature is lower than 150° C., drying time becomes excessively long and physical properties of a finally prepared superabsorbent polymer may decline, and when the drying temperature is higher than 250° C., only the polymer surface is excessively dried, which may cause fine powder generation in a milling process to be carried out later on, and physical properties of a finally prepared superabsorbent polymer may decline. Meanwhile, the drying time is not limited in the constitution, however, the drying may be carried out for 20 minutes to 90 minutes considering process efficiency and the like.

A drying method in such a drying step may also be selected and used without limit in the constitution as long as the method is commonly used as a drying process of hydrogel phase polymers. Specifically, the drying process may be carried out using methods such as hot air supply, infrared irradiation, microwave irradiation or ultraviolet radiation. Moisture content of the polymer after going through such a drying process may be from 0.1% by weight to 10% by weight.

After that, the method for preparing a superabsorbent polymer according to the present invention goes through a step of f) milling the dried polymer after going through the drying step. Particle sizes of the polymer obtained after the milling step are preferably from 150 μm to 850 μm. For this, a step of obtaining the superabsorbent polymer having particle sizes of 150 μm to 850 μm through sorting may be further included after the milling in the f) step. In such a sorting process, various meshes may be used as necessary for the sorting, however, meshes of #20 to 100# may be preferably used for the sorting. In the method for preparing a superabsorbent polymer according to the present invention, a pin mill, a hammer mill, a screw mill, a roll mill, a disc mill, a jog mill or the like may be specifically used a mill used for milling to such particle sizes, however, the mill is not limited thereto.

After that, the method for preparing a superabsorbent polymer according to the present invention goes through a step of g) adding a surface crosslinking agent to the milled hydrogel phase polymer.

The surface crosslinking agent added in the method for preparing a superabsorbent polymer according to the present invention is not limited in the constitution as long as it is a compound capable of reacting with a functional group included in the polymer. As the surface crosslinking agent, one or more types selected from the group consisting of polyalcohol compounds; epoxy compounds; polyamine compounds; haloepoxy compounds; condensates of haloepoxy compounds; oxazoline compounds; mono-, di- or polyoxazolidinone compounds; cyclic urea compounds; multivalent metal salts; and alkylene carbonate compounds may be preferably used in order to enhance properties of the produced superabsorbent polymer.

Specifically, examples of the polyalcohol compound may include one or more types selected from the group consisting of mono-, di-, tri-, tetra- or polyethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol and 1,2-cyclohexanedimethanol.

In addition, ethylene glycol diglycidyl ether, glycidol and the like may be used as the epoxy compound, and as the polyamine compound, one or more types selected from the group consisting of ethylenediamine, diethylenetriamine, triethylenetetraamine, tetraethylenepentamine, pentaethylenehexamine, polyethyleneimine and polyamide polyamine may be used.

As the haloepoxy compound, epichlorohydrin, epibromohydrin and α-methyl epichlorohydrin may be used. Meanwhile, examples of the mono-, di- or polyoxazolidinone compound may include 2-oxazolidinone and the like. As the alkylene carbonate compound, ethylene carbonate and the like may be used. These may be used either alone or as a combination thereof. Meanwhile, in order to increase efficiency of the surface crosslinking process, one or more types of polyalcohol compounds among these surface crosslinking agents may be preferably included and used, and more preferably, polyalcohol compounds having 2 to 10 carbon atoms may be used.

Content of the surface crosslinking agent mixed and added for surface treating the polymer particles may be properly specifically selected depending on the types of the added surface crosslinking agent or the reaction condition, however, the content of 0.001 parts by weight to 5 parts by weight, preferably 0.01 parts by weight to 3 parts by weight and more preferably 0.05 parts by weight to 2 parts by weight may be normally used with respect to 100 parts by weight of the polymer.

When the content of the surface crosslinking agent is too low, the surface crosslinking reaction hardly occurs, and when the content is greater than 5 parts by weight with respect to 100 parts by weight of the polymer, physical properties of the superabsorbent polymer may decline due to an excessive surface crosslinking reaction.

Herein, the method of adding the surface crosslinking agent to the polymer is not limited in the constitution, and a method of placing the surface crosslinking agent and the polymer powder in a reactor and mixing the result, a method of spraying the surface crosslinking agent on the polymer powder, a method of continuously supplying the polymer and the crosslinking agent to a reactor such as a mixer continuously operated and mixing the result, and the like, may be used.

After that, the method for preparing a superabsorbent polymer according to the present invention goes through a step of h) carrying out a surface crosslinking reaction.

According to another embodiment of the present invention, a temperature of the polymer itself may be preferably from 20° C. to 80° C. when adding the surface crosslinking agent in order to raise a temperature to the reaction temperature within 1 minute to 60 minutes for the surface crosslinking reaction after adding the surface crosslinking agent. In order to have such a polymer temperature, a process carried out after the drying step, which is carried out at a relatively high temperature, is continuously carried out, and process time may be shortened or the polymer may be separately heated when the process time is difficult to be shortened.

In addition, in the method for preparing a superabsorbent polymer according to the present invention, the surface crosslinking agent itself added to the polymer may be heated so as to raise a temperature to the reaction temperature within 1 minute to 60 minutes for the surface crosslinking reaction after adding the a surface crosslinking agent Meanwhile, the method for preparing a superabsorbent polymer according to the present invention is capable of improving efficiency of the surface crosslinking process when carrying out the surface crosslinking reaction after raising a temperature to the reaction temperature within 1 minute to 60 minutes for the surface crosslinking reaction, and consequently, a superabsorbent polymer having excellent physical properties may be obtained while minimizing residual monomer content of the finally obtained superabsorbent polymer. Herein, the temperature of the added surface crosslinking agent may be adjusted to a temperature from 5° C. to 60° C. and more preferably from 10° C. to 40° C. When the temperature of the surface crosslinking agent is lower than 5° C., an effect of reducing the rate of temperature raise to the temperature of the surface crosslinking reaction obtained by raising the temperature of the surface crosslinking agent is insignificant, and when the temperature of the surface crosslinking agent is higher than 60° C., the surface crosslinking agent may not be evenly distributed in the polymer. In the whole specification, the temperature of the surface crosslinking reaction may be defined as the whole temperature of the surface crosslinking agent added for the crosslinking reaction and the polymer.

Means to raise the temperature for the surface crosslinking reaction is not limited in the constitution. Specifically, means such as supplying a heating medium or direct heating with electricity or the like may be used, however, the present invention is not limited to the examples described above. Specific examples of a heat source capable of being used may include steam, electricity, ultraviolet rays, infrared rays and the like, and a heated thermal fluid and the like may also be used.

Meanwhile, in the method for preparing a superabsorbent polymer according to the present invention, the crosslinking reaction may be carried out for 1 minute to 60 minutes, preferably for 5 minutes to 40 minutes and most preferably for 10 minutes to 20 minutes after raising a temperature for the crosslinking reaction. When the crosslinking reaction time is excessively short of less than 1 minute, the crosslinking reaction may not sufficiently occur, and when the crosslinking reaction time is longer than 60 minutes, physical properties of a superabsorbent polymer may decline due to the excessive surface crosslinking reaction, and polymer crushing may occur due to prolonged stay in the reactor.

Hereinafter, the present invention will be described in more detail based on examples, however, embodiments disclosed below are for illustrative purposes only, and the scope of the present invention is not limited to these embodiments. The scope of the present invention is presented in the claims, and moreover, includes all modifications within the meaning and the scope equivalent to the descriptions in the claims. In addition, "%" and "parts" representing content in the following examples and comparative examples are based on a mass unless particularly specified otherwise.

EXAMPLE

Preparation Example

Preparation of Hydrogel Phase Polymer

A monomer mixture was prepared by mixing 100 g of acrylic acid, 0.3 g of polyethylene glycol diacrylate as a crosslinking agent, 0.033 g of diphenyl(2,4,6-trimethylbenzoyl)-phosphine oxide as an initiator, 38.9 g of caustic soda (sodium hydroxide, NaOH) and 103.9 g of water. After that, the monomer mixture was introduced on a continuously moving conveyer belt, ultraviolet rays (irradiation intensity: 2 mW/cm$^2$) was irradiated thereon, and UV polymerization was carried out for 2 minutes to obtain a hydrogel polymer.

EXAMPLE

Preparation of Superabsorbent Polymer

Example 1

The hydrogel phase polymer prepared according to the preparation example was chopped to a size of 5 mm×5 mm. To the chopped hydrogel phase polymer, porous superhydrophobic fine particle Silica Aerogel (AeroZel™, manufactured by HOS) was treated in 600 ppm with respect to the weight of a dried superabsorbent polymer. Then, the result was dried for 2 hours in a hot-air dryer at a temperature of 170° C., milled using a pin mill, and as a result, a superabsorbent polymer having particle diameters of 150 μm to 850 μm was obtained using a sieve. After 100 g of the sorted superabsorbent polymer having particle diameters of 150 μm to 850 μm was weighed and mixed for 60 seconds at 1000 RPM, 3.52 g of a surface crosslinking agent (3.0 g of water, 0.3 g of ethylene carbonate, 0.22 g of oxalic acid) was introduced thereto, and the result was mixed for 60 seconds. After that, the mixture was dried for 35 minutes in an oven at 192° C. to obtain an unmilled superabsorbent polymer, and again, particle sizes of the unmilled superabsorbent polymer were measured, the unmilled superabsorbent polymer was milled using a pin mill, and a superabsorbent polymer having particle sizes of 150 μm to 850 μm was obtained using a sieve. The Aerogel used above had particle sizes of 5 urn, a BET specific surface area of 700 m²/g, a contact angle of 144° for water and porosity of 95%.

The particle sizes of the Aerogel were measured and analyzed in accordance with the ISO 13320 by laser diffraction using a Helium-Neon Laser Optical System (HELOS). The BET specific surface area and the porosity were measured using a BET analyzer. The contact angle for water was measured using a contact angle analyzer (KRUSS DSA100). Specifically, a double-sided tape was applied on a flat glass plate and then fine particles were coated thereon to a monolayer, and when 5 μl of ultrapure water was placed on the monolayer, the ultrapure water was placed in a drop form, and the angle formed between the water drop and the glass plate was repeatedly measured 4 times and then an average value was calculated.

Example 2

A superabsorbent polymer was obtained in the same manner as in Example 1 except that the Silica Aerogel was used in 1000 ppm.

Example 3

A superabsorbent polymer was obtained in the same manner as in Example 1 except that the Silica Aerogel was used in 2500 ppm.

Example 4

A superabsorbent polymer was obtained in the same manner as in Example 1 except that the Silica Aerogel was used in 5000 ppm.

Comparative Example 1

A superabsorbent polymer having particle sizes of 150 μm to 850 μm was obtained in the same manner as in Example 1 except that the porous superhydrophobicity fine particle Silica Aerogel (AeroZel™, manufactured by JIOS) was not introduced, and 3.0 g of water, 3.5 g of methanol, 0.3 g of ethylene carbonate and 0.22 g of oxalic acid were introduced as the surface crosslinking agent.

Comparative Example 2

A superabsorbent polymer having particle sizes of 150 μm to 850 μm was obtained in the same manner as in Example 1 except that the porous superhydrophobicity fine particle Silica Aerogel (AeroZel™, manufactured by HOS) was not introduced.

Test Example

Physical Property Evaluation

Tests were performed as follows in order to evaluate physical properties of the superabsorbent polymers according to Examples 1 to 4 and Comparative Examples 1 and 2.

Test Example 1

Identification of Superabsorbent Polymer Particle Size Distribution

Particle size distribution for the superabsorbent polymers of Examples 1 to 4 and Comparative Examples 1 and 2 was identified. Particle sizes of the superabsorbent polymers were measured in accordance with the EDANA method WSP 240.3. 100 g of the superabsorbent polymer was divided using 850 μm 600 μm, 300 μm and 150 μm Pan Mesh, was vibrated for 10 minutes with an amplitude of 1.0 mm and a frequency of 50 Hz, and the content was measured as a residence amount at the top of each sieve. The results are shown in Table 1 and FIG. 1.

TABLE 1

| | | Particle Size Distribution (%) | | | |
|---|---|---|---|---|---|
| | Surface Crosslink | 150 μm or Less | 150 μm to 850 μm | 850 μm or Greater | Fine Particles |
| Example 1 | Before | 15.6 | 78.0 | 6.4 | 600 ppm |
| | After | 0.3 | 87.6 | 12.1 | 600 ppm |
| Example 2 | Before | 14.8 | 78.4 | 6.8 | 1000 ppm |
| | After | 0.3 | 90.3 | 9.5 | 1000 ppm |
| Example 3 | Before | 11.6 | 82.2 | 6.2 | 2500 ppm |
| | After | 0.2 | 90.6 | 9.2 | 2500 ppm |
| Example 4 | Before | 18.4 | 74.0 | 7.6 | 5000 ppm |
| | After | 0.2 | 92.7 | 7.0 | 5000 ppm |
| Comparative Example 1 | Before | 15.7 | 79.7 | 4.6 | 0 ppm |
| | After | 0.6 | 96.4 | 3.1 | 0 ppm |
| Comparative Example 2 | Before | 15.6 | 79.8 | 4.6 | 0 ppm |
| | After | 0.4 | 84.8 | 14.8 | 0 ppm |

Test Example 2

Absorption Under Pressure (AUP)

Absorption under pressure for the superabsorbent polymers of Examples 1 to 4 and Comparative Examples 1 and 2 was measured. The absorption under pressure was measured in accordance with the EDANA method WSP 241.3. Among the prepared superabsorbent polymer, 0.9 g of the sample having particle sizes of 150 μm to 850 μm was placed in a cylinder defined in the EDANA, and a pressure of 0.7 psi was applied using a piston and a weight. After that, the amount absorbing a 0.9% salt water solution for 60 minutes was measured, and the results are shown in Table 2 and FIG. 2.

TABLE 2

|  | Surface Crosslink | Absorption under Pressure (g/g) | Fine Particles |
|---|---|---|---|
| Example 1 | Before | 7.0 | 600 ppm |
|  | After | 20.6 | 600 ppm |
| Example 2 | Before | 7.1 | 1000 ppm |
|  | After | 20.5 | 1000 ppm |
| Example 3 | Before | 6.7 | 2500 ppm |
|  | After | 16.8 | 2500 ppm |
| Example 4 | Before | 6.5 | 5000 ppm |
|  | After | 15.4 | 5000 ppm |
| Comparative Example 1 | Before | 7.0 | 0 ppm |
|  | After | 19.5 | 0 ppm |
| Comparative Example 2 | Before | 7.0 | 0 ppm |
|  | After | 18.2 | 0 ppm |

Test Example 3

Permeability (Sec)

Permeability for the superabsorbent polymers of Examples 1 to 4 and Comparative Examples 1 and 2 was measured. Water was inversely introduced to a chromatography tube so that bubbles are not generated between a glass filter and a cork at the bottom of the chromatography tube, filling the tube for approximately 10 ml, and the chromatography tube was washed 2 to 3 times with salt water and filled with 0.9% salt water up to 40 ml or greater. In order to perform a blank test, a piston was introduced to the chromatography tube, a valve at the bottom was opened, and then the time taken for the liquid surface moving from a 40 ml mark line to a 20 ml mark line was recorded (B: sec). Among the prepared superabsorbent polymer, 0.2 g of the sample having particle sizes of 300 µm to 600 µm was placed therein, and salt water was added thereto so that the total salt water amount became 50 ml, and then the result was left attended for 30 minutes so that the superabsorbent polymer was sufficiently swollen. After that, a piston with a weight (0.3 psi) was introduced to the chromatography tube, and the result was left unattended for 1 minute. After opening a stopper at the bottom of the chromatography tube, the time taken for the liquid surface moving from a 40 ml mark line to a 20 ml mark line was recorded (T1: sec). Through the following Mathematical Formula 1, the results are shown in Table 3 and FIG. 3.

$$\text{Permeability}=T1-B \qquad \text{[Mathematical Formula 1]}$$

TABLE 3

|  | Permeability (sec) | Fine Particles |
|---|---|---|
| Example 1 | 784 | 600 ppm |
| Example 2 | 593 | 1000 ppm |
| Example 3 | 509 | 2500 ppm |
| Example 4 | 404 | 5000 ppm |
| Comparative Example 1 | 746 | 0 ppm |
| Comparative Example 2 | 1335 | 0 ppm |

From the results of Table 1 and FIG. 1, it was identified that differences in the particle size distribution between Comparative Examples 1 and 2 and Examples 1 to 4 were less than 10%. However, when examining changes in the particle size distribution after sampling particles having particle sizes of 150 µm to 850 µm only and surface crosslinking the result, Comparative Example 2 that did not use an organic solvent (MeOH) in the crosslinking liquid was identified to have more aggregated particles having particle sizes of 850 µm or greater by closer to 15% compared to Comparative Example 1 using an organic solvent (MeOH), let alone Examples 1 to 4.

Having an increased number of particles with particle sizes of 850 µm or greater means the surface crosslinking liquid being not able to evenly spread. Actually, surface crosslinking was not evenly accomplished in Comparative Example 2, and therefore, it was identified from Table 2 and FIG. 2 that the absorption under pressure property declined, and it was also identified from Table 3 and FIG. 3 that the permeability property highly declined.

In addition, in Examples 1 to 4, 600 ppm to 5000 ppm of the superhydrophobic fine particles were pretreated and then crosslinked, and as a result, a generally even crosslinking effect was able to be obtained when compared to Comparative Example 2, and particularly when the content of the superhydrophobicity fine particles was approximately from 600 ppm to 1000 ppm as in Examples 1 and 2, it was seen that more enhanced absorption under pressure was able to be obtained compared to the absorption under pressure of Comparative Example 1 and Comparative Example 2 using an existing surface crosslinking liquid.

It was also seen that equal or higher performance was obtained in the absorption under pressure and the permeability in Examples 1 to 4 compared to Comparative Example 1 even with half the amount of the surface crosslinking liquid introduced.

Accordingly, it was seen that, by evenly distributing superhydrophobic fine particles prior to the surface crosslinking process of the superabsorbent polymer, particle agglomeration during the crosslinking was prevented, and the total crosslinking liquid amount was capable of being reduced by 50% or greater as well.

The invention claimed is:

1. A method for preparing a superabsorbent polymer comprising:
    a) preparing a hydrogel phase polymer by thermopolymerizing or photopolymerizing a monomer composition including a water-soluble ethylenically unsaturated monomer and a polymerization initiator;
    b) chopping the hydrogel phase polymer to form a chopped hydrogel phase polymer;
    c) adding particles to the chopped hydrogel phase polymer to form a particle-added hydrogel phase polymer, wherein the particles have a i) BET specific surface area of 300 $m^2/g$ to 1500 $m^2/g$ and ii) porosity of 50% or greater;
    d) chopping the particle-added hydrogel phase polymer again to form an additionally chopped hydrogel phase polymer;
    e) drying the additionally chopped hydrogel phase polymer to form a dried hydrogel phase polymer;
    f) milling the dried hydrogel phase polymer to form a milled hydrogel phase polymer;
    g) adding a surface crosslinking agent to the milled hydrogel phase polymer; and
    h) carrying out a surface crosslinking reaction, wherein the surface crosslinking agent does not contain an organic solvent.

2. The method for preparing a superabsorbent polymer of claim 1, wherein the particles have particle sizes of 2 nm to 50 µm.

3. The method for preparing a superabsorbent polymer of claim 1, wherein the particles have superhydrophobicity with a contact angle of 125° or greater for water.

4. The method for preparing a superabsorbent polymer of claim 1, wherein the particles have particle sizes of 2 nm to 50 μm and have superhydrophobicity with a contact angle of 125° or greater for water.

5. The method for preparing a superabsorbent polymer of claim 1, wherein the particles have a BET specific surface area of 500 m$^2$/g to 1500 m$^2$/g.

6. The method for preparing a superabsorbent polymer of claim 1, wherein the particles have a BET specific surface area of 700 m$^2$/g to 1500 m$^2$/g.

7. The method for preparing a superabsorbent polymer of claim 3, wherein the particles have superhydrophobicity with a contact angle of 140° or greater for water.

8. The method for preparing a superabsorbent polymer of claim 3, wherein the particles have superhydrophobicity with a contact angle of 145° or greater for water.

9. The method for preparing a superabsorbent polymer of claim 1, wherein the particles have porosity of 90% or greater.

10. The method for preparing a superabsorbent polymer of claim 1, wherein the particles are included in 0.001 parts by weight to 1 part by weight with respect to 100 parts by weight of the dried superabsorbent polymer.

11. The method for preparing a superabsorbent polymer of claim 1, wherein the particles are one or more types selected from the group consisting of silica, alumina, carbon and titania ($TiO_2$).

12. The method for preparing a superabsorbent polymer of claim 1, further comprising obtaining a superabsorbent polymer having a size of 150 μm to 850 μm through sorting after the milling of the f).

13. The method for preparing a superabsorbent polymer of claim 1, wherein the drying of the e) is carried out at a temperature of 150° C. to 250° C.

14. The method for preparing a superabsorbent polymer of claim 1, wherein the surface crosslinking agent of the g) is any one or more selected from the group consisting of polyalcohol compounds; epoxy compounds; polyamine compounds; haloepoxy compounds; condensates of haloepoxy compounds; oxazoline compounds; mono-, di- or polyoxazolidinone compounds; cyclic urea compounds; multivalent metal salts; and alkylene carbonate compounds.

15. The method for preparing a superabsorbent polymer of claim 1, wherein the surface crosslinking agent of the g) is added in 0.001 parts by weight to 5 parts by weight with respect to 100 parts by weight of the milled hydrogel phase polymer.

16. The method for preparing a superabsorbent polymer of claim 1, wherein, in the g), the milled hydrogel phase polymer has a surface temperature of 60° C. to 90° C.

17. The method for preparing a superabsorbent polymer of claim 1, wherein, in the g), the added surface crosslinking agent has a temperature of 5° C. to 40° C.

18. The method for preparing a superabsorbent polymer of claim 1, wherein, in the h), the surface crosslinking reaction is carried out for 10 minutes to 120 minutes.

19. The method for preparing a superabsorbent polymer of claim 1, wherein, in the h), any one or more selected from the heat source group consisting of steam, electricity, ultraviolet rays and infrared rays are irradiated to raise a temperature.

20. The method for preparing a superabsorbent polymer of claim 1, further comprising milling the superabsorbent polymer again to particle sizes of 150 μm to 850 μm after the surface crosslinking reaction of the h).

* * * * *